(12) United States Patent
Kojima et al.

(10) Patent No.: US 7,373,903 B2
(45) Date of Patent: May 20, 2008

(54) MEDICAL WASTE TREATMENT APPARATUS

(75) Inventors: Kazuo Kojima, Shiga (JP); Koutarou Mine, Shiga (JP); Kiyohiro Furuno, Shiga (JP); Takatoshi Kanou, Shiga (JP)

(73) Assignee: Natsuhara Corporation, Shiga (JP)

( * ) Notice: Subject to any disclaimer, the term of this patent is extended or adjusted under 35 U.S.C. 154(b) by 81 days.

(21) Appl. No.: 10/588,121

(22) PCT Filed: Feb. 4, 2004

(86) PCT No.: PCT/JP2004/001151

§ 371 (c)(1),
(2), (4) Date: Aug. 1, 2006

(87) PCT Pub. No.: WO2005/075119

PCT Pub. Date: Aug. 18, 2005

(65) Prior Publication Data

US 2007/0157860 A1   Jul. 12, 2007

(51) Int. Cl.
*B09B 3/00* (2006.01)

(52) U.S. Cl. .......... 122/482; 110/235; 110/346

(58) Field of Classification Search ........ 122/7 R, 122/459, 482, 485, 487; 110/203, 210–216, 110/250–257, 314, 341–346, 235
See application file for complete search history.

(56) References Cited

U.S. PATENT DOCUMENTS 3,875,357 A * 4/1975 Foster et al. ............ 210/758
4,863,702 A * 9/1989 Galloway et al. ........ 422/189
5,348,235 A * 9/1994 Pappas .................... 241/41
5,809,911 A * 9/1998 Feizollahi ................ 110/346
6,250,236 B1 * 6/2001 Feizollahi ................ 110/346

FOREIGN PATENT DOCUMENTS

JP    11128870 A  *  5/1999
JP   2004129993 A  *  4/2004

* cited by examiner

*Primary Examiner*—Gregory A. Wilson
(74) *Attorney, Agent, or Firm*—Milde & Hoffberg, LLP

(57) ABSTRACT

A medical waste treatment apparatus which comprises:
- a processing chamber where medical waste is loaded and heated;
- a combustion chamber having fuel burning means for burning a fuel to produce superheated water vapor by heating one of water and steam;
- superheated water vapor supply means having the combustion chamber for supplying the superheated water vapor to the processing chamber;
- a jacket surrounding at least a part of the processing chamber and forming a jacket space surrounding at least a part of the processing chamber between outer walls of the processing chamber; and
- a combustion gas introduction path interposed between the jacket and the combustion chamber for introducing combustion gas generated by the fuel burning means into the jacket space.

14 Claims, 1 Drawing Sheet

MEDICAL WASTE TREATMENT APPARATUS

TECHNICAL FIELD OF THE INVENTION

The present invention relates to a treatment apparatus for medical waste, such as used injection needles and drip packs.

BACKGROUND OF THE INVENTION

Medical waste is sterilized and disposed. Conventionally, methods for applying steam and treating with an autoclave or treating with gases, such as formalin gas and ethylene oxide gas, or the like have been used as sterilization methods. However, there are fears of an incomplete sterilization when applying only live steam to medical waste and in addition, in many cases, a portion of the medical waste is decomposed or volatized by the application of steam, which may cause a bad odor and toxic components, so that such bad odor and toxic components become problems. Since a high-pressured container is used for an autoclave, the autoclave is so large-scale that its safety management is troublesome. Gas treatment is costly from the viewpoint of its apparatus and management in measures against leakage of gases because gases are harmful to body. Recent medical waste in various shapes may make it difficult to be dealt with after such sterilization treatment.

SUMMARY OF THE INVENTION

In view of these problems, it is an object of the present invention to provide a medical waste treatment apparatus which is compact in size with little bad odor and is easy to be disposed after sterilization treatment.

A medical waste treatment apparatus of the present invention comprises: a processing chamber where medical waste is loaded and heated; a combustion chamber having fuel burning means for burning a fuel to produce superheated water vapor by heating one of water and steam; superheated water vapor supply means having the combustion chamber for supplying superheated water vapor to the processing chamber; a jacket surrounding at least a part of the processing chamber and forming a jacket space surrounding at least a part of the processing chamber between outer walls of the processing chamber; and a combustion gas introduction path interposed between the jacket and the combustion chamber for introducing combustion gas generated by the fuel burning means into the jacket space.

The medical waste treatment apparatus may comprise an exhaust gas introduction path interposed between the processing chamber and the combustion chamber for introducing exhaust gas generated by heating in the processing chamber with the superheated water vapor into the combustion chamber.

In the medical waste treatment apparatus, a catalyst for promoting the burning of the exhaust gas by coming into contact with the exhaust gas may be placed in the combustion gas introduction path.

The superheated water vapor supply means may comprise: a hose provided in the combustion chamber and heated by the combustion gas; and water supply means for supplying water to the hose.

The medical waste treatment apparatus may comprise jacket air introduction means for introducing air to cool the outer walls of the processing chamber after the completion of heating the medical waste into the jacket space.

The medical waste treatment apparatus may comprise processing chamber air introduction means for introducing air into the processing chamber after the completion of heating the medical waste.

The medical waste treatment apparatus may comprise: stirring means for stirring the medical waste in the processing chamber; discharging means for discharging the medical waste heated and stirred in the processing chamber from the bottom of the processing chamber; and a recovery container where the medical waste heated and stirred in the processing chamber is loaded.

The medical waste treatment apparatus may comprise container air introduction means for introducing air into the recovery container where the medical waste is loaded.

The medical waste treatment apparatus may comprise: jacket air introduction means for introducing air to cool the outer walls of the processing chamber after the completion of heating the medical waste into the jacket space; processing chamber air introduction means for introducing air into the processing chamber after the completion of heating the medical waste; a recovery container where the medical waste loaded into the processing chamber to be heated and stirred is discharged from the processing chamber and is loaded; and container air introduction means for introducing air into the recovery container, wherein the jacket air introduction means, the container air introduction means, and the processing chamber air introduction means may share one blower.

A fuel for one of blast furnace and thermal power generation of the present invention consists of medical waste treated by the medical waste treatment apparatus.

DESCRIPTION OF THE PREFERRED EMBODIMENTS

Figure 1:
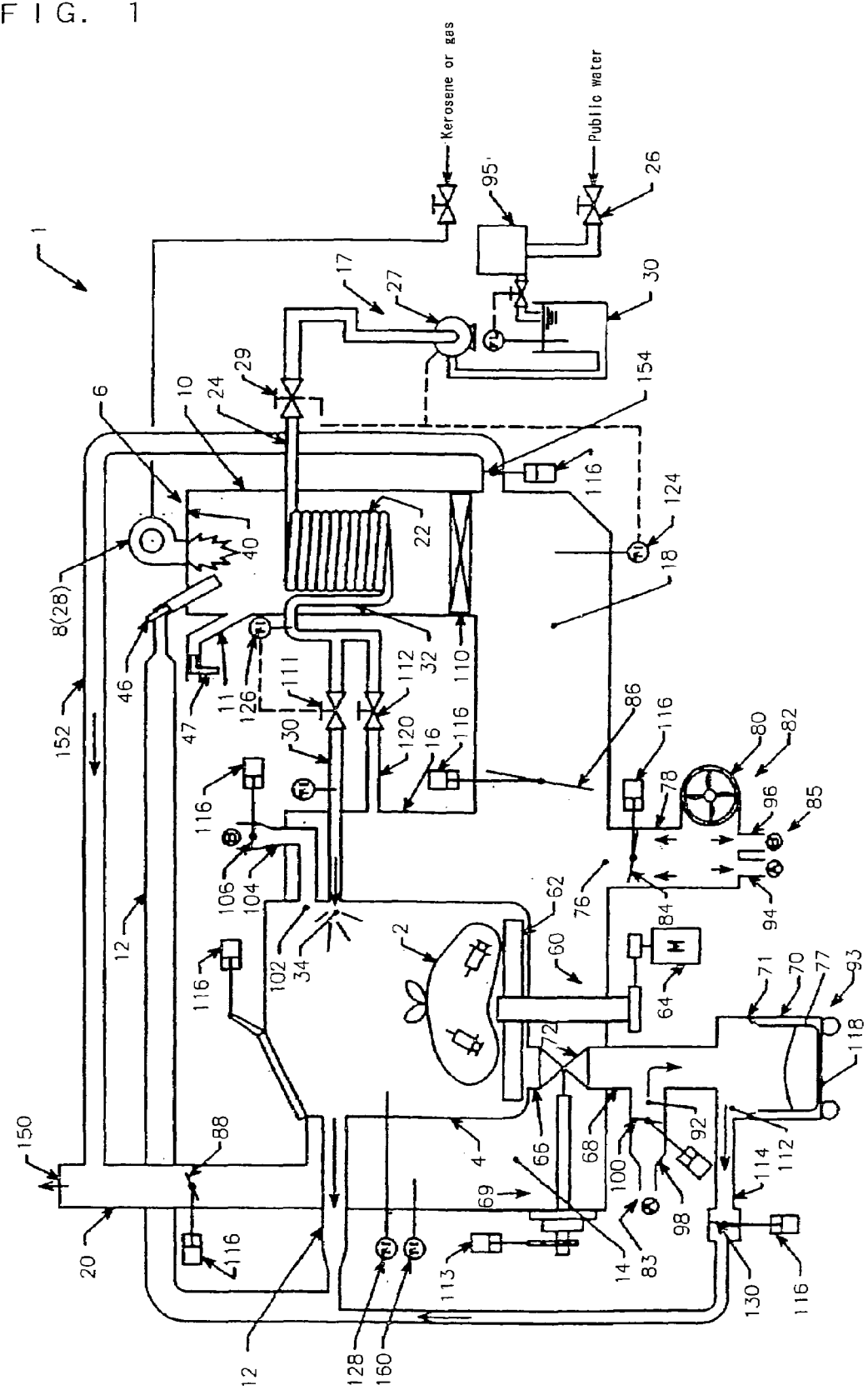
FIG. 1 is a block diagram illustrating the configuration of a medical waste treatment apparatus according to the present invention.

A preferred embodiment of the present invention will now be described in detail on the basis of the accompanying drawing. FIG. 1 is a view illustrating the configuration to show one example of the configuration of a medical waste treatment apparatus according to the present invention. In FIG. 1, a medical waste treatment apparatus 1 of the present invention comprises: a processing chamber 4 where medical waste 2 is loaded and heated; and superheated water vapor supply means 6 for supplying superheated water vapor to the processing chamber 4. The superheated water vapor supply means 6 comprises a combustion chamber 10 having fuel burning means 8 for producing superheated water vapor. The medical waste treatment apparatus 1 further comprises a jacket 16 for surrounding the processing chamber 4 and forming jacket space 14 surrounding the processing chamber 4 between outer walls of the processing chamber 4.

The superheated water vapor supply means 6 has a hose 22 wound in the spiral state, and water is supplied to the hose 22 from one end 24. Water is public water or water passes through a water-supply valve 26 connected to a water source prepared and then passes through a soft water unit 95 to be changed into soft water, if necessary, to be supplied to the hose 22 from a water-supply pump 27 through a reservoir 30. Water supply means 17 for supplying water to the hose 22 comprises: the water-supply valve 26; the soft water unit 95; the reservoir 30; the water-supply pump 27; and a soft water valve 29. Water in the hose 22 is heated by a burner 28 which is the fuel burning means 8 through tube walls of the hose 22 to be steam and is further heated to be superheated water vapor. Another end 32 of the hose 22 is in continuity through the inside of the processing chamber 4 and a superheated water vapor introduction pipe 30 and superheated water vapor is introduced from a superheated water vapor outburst outlet 34 provided in the processing roam 4 at a tip of the superheated water vapor introduction pipe 30 into the processing chamber 4. The superheated water vapor introduction pipe 30 has a superheated water vapor valve 111.

A portion heated by the burner 28 of the hose 22 is housed in a combustion chamber 10. The burner 28 is arranged on an upper wall 40 of the combustion chamber 10. A fuel is burned by the burner 28 and combustion gas is spouted inside the combustion chamber 10.

The combustion chamber 10 is in continuity with the jacket space 14 in the lower part through a combustion gas introduction path 18. This introduces combustion gas generated by the burner 28 into the jacket space 14 through the combustion gas introduction path 18, so that the processing chamber 4 is heated or kept warm by the heat of the combustion gas through the outer walls of the processing chamber 4.

On the other hand, an exhaust gas introduction path 12 for introducing exhaust gas generated from the medical waste 2 heated by superheated water vapor introduced into the processing chamber 4 into the combustion chamber 10 is interposed between the combustion chamber 10 and the processing chamber 4. Exhaust gas is received by an ejector 46 for exhaust gas provided at an outlet of the exhaust gas introduction path 12 and is introduced into the combustion chamber 10 to be burned with the fuel by the burner 28. This burning significantly reduces a bad smell of the exhaust gas.

On the other hand, in the combustion chamber 10, an external air introduction port 11 for introducing external air into the combustion chamber 10 is provided near the outlet of combustion gas emitted from the burner 28 and external air is introduced into the combustion chamber 10 by an air introduction ejector 47, which leads to the promotion of combustion gas in the combustion chamber 10 and exhaust gas fed from the processing chamber 4 being burned.

A superheated water vapor introduction path 120 for introducing superheated water vapor into the jacket space 14 is connected to the jacket 16. The superheated water vapor introduction path 120 has a superheated water vapor valve 112 and there is a branch near another end 32 of the hose 22 divided into the superheated water vapor valve 112 and the superheated water vapor introduction pipe 30.

Further, the jacket 16 has a discharge duct 20 for emitting gases introduced into the jacket space 14 to outside. Moreover, the jacket 16 has a combustion gas re-introduction path for re-introducing combustion gas introduced into the jacket space 14 into the combustion chamber 10, which is not shown in the figure.

The processing chamber 4 includes stirring means 60 having a stirring fan 62 disposed at the inner bottom, in which the medical waste 2 in the process of heat treatment and heat-treated medical waste are stirred. The stirring fan 62 is driven by a stirring motor 64 and rotates in a horizontal direction.

An opening 66 is made at the bottom of the processing chamber 4. The opening 66 is in continuity with a discharge duct 68 extending downward. A recovery container 70 is provided just below the discharge duct 68. A transportable container 77 is fitted into the recovery container 70, if necessary.

The medical waste reduced by heat treatment is transferred from the opening 66 to drop in the recovery container 70 or the transportable container 77 through the discharge duct 68 by the rotation of the stirring fan 62. Opening and closing means 69 for opening and closing the discharge duct 68 in accordance with the timing when the heat-treated medical waste is discharged is provided in the upper portion of the discharge duct 68. The opening and closing means 69 comprises a shutter 72 having a cylinder 113 for driving. Discharging means 93 for discharging the heat-treated medical waste into the recovery container 70 comprises the opening 66, the opening and closing means 69, and the discharge duct 68.

In addition, an introduction port 76 for introducing external air into the jacket space 14 is provided in the jacket 16. Air is introduced into the jacket space 14 from the introduction port 76 when the heating of the medical waste is completed and then outer walls of the processing chamber 4 are cooled, which results in cooling of the inside of the processing chamber 4.

Air is introduced into the jacket space 14 by jacket air introduction means 82 having a blower 80. A jacket cooling port damper 84 attached to an introduction port duct 78 being in continuity with the introduction port 76 is opened when the heating of the medical waste is completed. Air is introduced from the blower 80 into the jacket space 14 through the introduction port duct 78. At that time, a damper 86 between the combustion roam and the jacket provided in the combustion gas introduction path 18 is closed. And a discharge duct damper 88 attached to the discharge duct 20 is opened.

Furthermore, air is introduced into the recovery container 70 through an outside air conducting port 92 provided in the middle part of the discharge duct 68 by container air introduction means 83 sharing the blower 80. The introduction port 76 continues to branching paths 94 and 96 branched downward. The branching path 94 is communicated with an inlet A of an outside air conducting duct 98 which leads to the outside air introduction port 92 through an outlet A. The outside air conducting duct 98 has an outside air conducting damper 100 which is opened when air is introduced.

The shutter 72 is closed when air is introduced into the recovery container 70. An air discharge outlet 112 for discharging introduced air is provided for the recovery container 70, so that air introduced into the recovery container 70 is discharged through an air discharge duct 114 communicated with the air discharge outlet 112. The odor generated by the medical waste in the recovery container 70 is mixed with the discharged air. Since the air discharge duct 114 is communicated with the exhaust gas introduction path 12, air mixed with the odor is introduced into the combustion chamber 10 through the exhaust gas introduction path 12.

Air is introduced inside the processing chamber 4 by processing chamber air introduction means 85 for sharing the blower 80. An air introduction port 102 is provided in the processing chamber 4 and an inlet B of an air introduction duct 104 which leads to the air introduction port 102 is communicated with an outlet B of the branching path 96. The air introduction duct 104 has an air introduction damper 106 which is opened when air is introduced.

A catalyst 110 is placed in the combustion gas introduction path 18. The catalyst 110 contains metals whose major component is platinum and promotes the burning of exhaust gas by coming into contact with exhaust gas, so that carbon monoxide, hydrocarbon, and other organic gas or the like contained in exhaust gas are oxidized to be changed into water or harmless gas, such as carbon dioxide gas or the like. The kind of the catalyst 110 including the one available in the market is not particularly limited as long as having such functions.

The recovery container 70 is attachably and removably separable at a separating part 71 and a portable container 118 positioned in the lower portion is separable from the main body to be carried to another place after the treated medical waste is loaded. The portable container 118 is double-wall structured having the aforementioned transportable container 77 inside thereof, so that the treated medical waste that is the contents can be discharged after taking out the transportable container 77 only at an appropriate place.

The symbol 116 shows a cylinder for opening, closing, and driving the above-mentioned each damper attached to each place of the gas path of the medical waste treatment apparatus 1.

In the medical waste treatment apparatus 1 having such configuration, unlike a method for directly heating medical waste by a burner or the like, there is no such trouble that the medical waste starts burning by heating because of heating the medical waste by superheated water vapor. In addition, there is no fear of toxic and smelling gas being emitted to outside in volume because treatment gas generated from the heated medical waste is decomposed by being burned using a burner for generating superheated water vapor.

Toxic and smelling gas components are decomposed by effectively burning with the catalyst 110 placed in the combustion gas introduction path 18. Each kind of tube and container composed of each portion of the medical waste treatment apparatus 1 are preferably made of stainless steel in view of durability.

One example of operating procedures for the medical waste treatment apparatus 1 of the present invention will be described. The following operation can be automatically conducted by a sequencer or the like.

Opening and closing instruments, such as all dampers and valves or the like are in a closed state and actuators, such as a burner, a pump, and an ejector or the like are in a shutdown state or an off state before starting the operation. Loading medical waste into the processing chamber 4 and first of all ignite the burner 28 in the high combustion node, switch on the air introduction ejector 47, and then open the damper 86 between the combustion chamber and the jacket. Open the superheated water vapor valve 112 and close the superheated water vapor valve 111. The soft water valve 29 in the path where soft water is supplied to the hose 22 to actuate the water-supply pump 27 when the combustion temperature detected by a sensor 124 reaches a set point.

When the temperature of the another end 32 of the hose 22 detected by a sensor 126 reaches a set point, the superheated water vapor valve 112 is closed and the superheated water vapor valve 111 is opened, so that superheated water vapor starts to be introduced into the processing chamber 4. When the temperature in the processing chamber 4 detected by a sensor 128 reaches a set point, the stirring fan 62 is actuated. The stirring fan 62 repeats a normal rotation and a reverse rotation at prescribed time intervals. The set point is preferably 140 to 150° C. A shift between a high combustion node and a low combustion mode is made by the burner 28 based on the temperature in the jacket space 14 detected by a sensor 160 to keep the temperature in the jacket space 14 at a designated temperature during treatment.

After a predetermined treatment time, for example, 15 minutes later, the shutter 72 is opened, the superheated water vapor valve 112 is opened, and then the superheated water vapor valve 111 is closed.

After the lapse of a predetermined time, the blower 80 is actuated. A jacket cooling damper 84 is opened, the soft water valve 29 is closed, the burner 28 is in the low combustion mode, the shutter 72 is closed, the damper 88 attached to the discharge duct 20 is opened, a damper 154 of a combustion chamber duct 152 to lead to an outlet 150 is opened, the damper 106 of the air introduction duct 104 is opened, and the damper 86 between combustion chamber and jacket is closed, and the water-supply pump 27 stops.

After the closing of the shutter 72, the outside air conducting damper 100 is opened and the damper 130 attached to the air discharge duct 114 is opened.

The burner 28 is extinguished after continuing its operation in a low combustion state for a certain period of time, and a series of treatment procedures are completed when cooling to a prescribed temperature in the processing chamber, so that the opening and closing instruments, such as all of the dampers and valves or the like are in the closing state and all of the actuators, such as burners, pumps, and ejectors or the like return to the stop state or the off state. The medical waste treated and released into the recovery container 70 is recovered after a series of such treatment procedures.

The medical waste treatment apparatus 1 of the present invention has excellent thermal efficiency in heat treatment of medical waste because the processing chamber 4 is kept warm by the introduction of combustion gas into the jacket space 14.

In the medical waste treatment apparatus 1 of the present invention, since exhaust gas generated by the heating of the medical waste with superheated water vapor is introduced into the combustion chamber 10 to be burned, the medical waste is decomposed by the combustion of exhaust gas, so that smelling and toxic components contained in exhaust gas are effectively removed without the use of an additional combustion apparatus or a filter to remove the smelling and the toxic components.

In the medical waste treatment apparatus 1 of the present invention, a foul smell is little generated when the recovery container 70 is carried and the medical waste is taken out because exhaust gas in the recovery container 70 is purged and the medical waste is cooled before the opening of the recovery container 70 to house the medical waste after treatment. Moreover, the operation of such purging and cooling can be easily performed by an automatic shift of the dampers.

In the medical waste treatment apparatus 1 of the present invention, a catalyst for promoting the combustion of exhaust gas by coming into contact with exhaust gas is placed in the combustion gas introduction path 18, so that exhaust gas is almost perfectly decomposed by burning.

The medical waste treatment apparatus 1 of the present invention may be a compact-size apparatus without the need for a large-scale live steam generator because of having superheated water vapor supply means for changing water into superheated water vapor by heating water on a first stage, which results in easy operation in such a manner that the medical waste treatment apparatus 1 is usable in a state of being directly connected to the hose of public water or a prepared water supply source.

In the medical waste treatment apparatus 1 of the present invention, the outer walls and the inside of the processing chamber 4 are cooled by the introduction of air into the processing chamber 4 after the completion of heating the medical waste, resulting in virtually no smell remains on the medical waste after the treatment. Thus, the cooling operation is easily performed by the automatic switch of the dampers.

In the medical waste treatment apparatus 1 of the present invention, the jacket air introduction means, the processing chamber air introduction means, and the container air introduction means share one blower 80, so that the introducing of air into the processing chamber 4, the jacket space 14 or the recovery container 70 can be switched by one blower 80, which enables to be compact sized.

The medical waste treatment apparatus 1 of the present invention may be preferably used for the treatment of medical waste containing plastics, such as injectors, drip packs, transfusion sets, tubes, gloves for surgery, gloves for treatment, test tubes, and ampoules or the like, rubber kinds, and glass.

While the aspects of the medical waste treatment apparatus according to the present invention have been described so far, it is to be understood that the present invention may be practiced in other embodiments in which various improvements, modifications, and variations are added based on the art of those skilled without departing from the spirit of the invention and any of these aspects fall within the scope of the present invention.

For example, the hose 22 may be a tube warped in the form of a switchback. Further, a well-known superheated water vapor generator having well-known heating means for heating water vapor may be used as the superheated water vapor supply means 6. The opening and closing means 69 may have an opening and closing valve and may have an openable and closable door-type masking shield which can be closed and opened in a passage of the discharge duct 68. The opening and closing means 69 is not particularly limited in its form as long as the medical waste is not hindered in its passing when opened after treatment in the passage of the discharge duct 68.

For example, the recovery container 70 may be constructed so as to be double-wall structured having the transportable container 77 inside, even though the recovery container 70 is not separable at the separating part 71 and have an outlet freely opened and closed to take out the transportable container 77. Alternatively, the recovery container 70 may be constructed so as to have an openable and closable outlet to directly remove by taking out the medical waste after the treatment.

The medical waste treated by the medical waste treatment apparatus of the present invention is a volume reduced solid. This solid has a possibility of being used as a fuel because a large amount of combustible materials, such as high polymer materials or the like are contained. However, toxic materials, such as dioxin or the like are generated by burning at relatively low temperatures, so that it was difficult to develop for commercial use as a fuel. As a result of repeated study, it has been turned out that the medical waste treated by the medical waste treatment apparatus of the present invention is preferably used as a fuel for blast furnace by mixing with other fuel. The medical waste has also been found out to be preferably used as a fuel for thermal power generation by mixing with other fuel. In either case, since dioxin discharged to outside after the burning is close to non-existent, other generated gases are effectively treated by exhaust treatment means fitted with a conventional combustor as well as gas generated by the other fuel.

The use of the medical waste treated by the medical waste treatment apparatus according to the present invention as a fuel for one of blast furnace and a fuel for thermal power generation makes it possible to reduce costs for raw materials, such as a fuel for blast furnace or a fuel for thermal power generation and needs no places and costs for burying the medical waste treated by the medical waste treatment apparatus of the present invention.

The medical waste treatment apparatus of the present invention is excellent in heating efficiency, easy to handle, and is also compact sized. In addition, there is little smelling and toxic components to be disbursed outside because the smelling and the toxic components are decomposed at the time of operation. The treatment apparatus is easy to treat waste after sterilization as well.

The medical waste treatment apparatus of the present invention is applicable to household garbage, building waste, waste related to food processing, incineration of general industrial waste as well as medical waste, which leads to materialize incineration with minimized generation of an odor or toxic components.

There has thus been shown and described a novel medical waste treatment apparatus which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A medical waste treatment apparatus comprising:
   a processing chamber where medical waste is loaded and heated;
   a combustion chamber having fuel burning means for burning a fuel to produce superheated water vapor by heating one of water and steam;
   superheated water vapor supply means having the combustion chamber for supplying superheated water vapor to the processing chamber;
   a jacket surrounding at least a part of the processing chamber and forming a jacket space surrounding at least a part of the processing chamber between outer walls of the processing chamber; and
   a combustion gas introduction path interposed between the jacket and the combustion chamber for introducing combustion gas generated by the fuel burning means into the jacket space.

2. The apparatus according to claim 1, further comprising an exhaust gas introduction path interposed between the processing chamber and the combustion chamber for introducing exhaust gas generated by heating in the processing chamber with the superheated water vapor into the combustion chamber.

3. The apparatus according to claim 1, wherein a catalyst for promoting the burning of the exhaust gas by coming into contact with the exhaust gas is provided in the combustion gas introduction path.

4. The apparatus according to claim 1, wherein the superheated water vapor supply means comprises: a hose provided in the combustion chamber and heated by the combustion gas; and water supply means for supplying water to the hose.

5. The apparatus according to claim 1, further comprising jacket air introduction means for introducing air to cool the outer walls of the processing chamber after the completion of heating the medical waste into the jacket space.

6. The apparatus according to claim 5, further comprising:
jacket air introduction means for introducing air to cool the outer walls of the processing chamber after the completion of heating the medical waste into the jacket space;
processing chamber air introduction means for introducing air into the processing chamber after the completion of heating the medical waste;
a recovery container where the medical waste loaded into the processing chamber to be heated and stirred is discharged from the processing chamber and is loaded; and
container air introduction means for introducing air into the recovery container,
wherein the jacket air introduction means, the container air introduction means, and the processing chamber air introduction means share one blower.

7. The apparatus according to claim 1, further comprising processing chamber air introduction means for introducing air into the processing chamber after the completion of heating the medical waste.

8. The apparatus according to claim 5, further comprising processing chamber air introduction means for introducing air into the processing chamber after the completion of heating the medical waste.

9. The apparatus according to claim 1, further comprising:
stirring means for stirring the medical waste in the processing room;
discharging means for discharging the medical waste heated and stirred in the processing chamber from the bottom of the processing chamber; and
a recovery container where the medical waste heated and stirred in the processing chambered is loaded.

10. The apparatus according to claim 9, further comprising container air introduction means for introducing air into the recovery container where the medical waste is loaded.

11. A fuel for one of blast furnace and thermal power generation comprising the medical waste treated by the medical waste treatment apparatus according to claim 9.

12. The apparatus according to claim 1, further comprising:
jacket air introduction means for introducing air to cool the outer walls of the processing chamber after the completion of heating the medical waste into the jacket space;
processing chamber air introduction means for introducing air into the processing chamber after the completion of heating the medical waste;
a recovery container where the medical waste loaded into the processing chamber to be heated and stirred is discharged from the processing chamber and is loaded; and
container air introduction means for introducing air into the recovery container,
wherein the jacket air introduction means, the container air introduction means, and the processing chamber air introduction means share one blower.

13. A fuel for one of blast furnace and thermal power generation comprising the medical waste treated by the medical waste treatment apparatus according to claim 12.

14. A fuel for one of blast furnace and thermal power generation comprising the medical waste treated by the medical waste treatment apparatus according to claim 1.

* * * * *